(12) United States Patent
Wright et al.

(10) Patent No.: US 12,090,196 B2
(45) Date of Patent: Sep. 17, 2024

(54) TRYPANOSOMAL VACCINE

(71) Applicant: GENOME RESEARCH LIMITED (GB/GB), Saffron Walden (GB)

(72) Inventors: Gavin Wright, Saffron Walden (GB); Delphine Autheman, Saffron Walden (GB)

(73) Assignee: GENOME RESEARCH LIMITED, Saffron Walden (GB)

( * ) Notice: Subject to any disclaimer, the term of this patent is extended or adjusted under 35 U.S.C. 154(b) by 460 days.

(21) Appl. No.: 17/420,982

(22) PCT Filed: Jan. 7, 2020

(86) PCT No.: PCT/GB2020/050022
§ 371 (c)(1),
(2) Date: Jul. 6, 2021

(87) PCT Pub. No.: WO2020/144464
PCT Pub. Date: Jul. 16, 2020

(65) Prior Publication Data
US 2022/0096613 A1    Mar. 31, 2022

(30) Foreign Application Priority Data
Jan. 7, 2019  (GB) .................................. 1900187

(51) Int. Cl.
*A61K 39/005* (2006.01)
*A61P 33/02* (2006.01)

(52) U.S. Cl.
CPC ............ *A61K 39/005* (2013.01); *A61P 33/02* (2018.01)

(58) Field of Classification Search
CPC .............................. A61P 33/02; A61K 39/005
See application file for complete search history.

(56) References Cited

U.S. PATENT DOCUMENTS

| | | |
|---|---|---|
| 2017/0296637 A1 | 10/2017 | Pleguezuelos Mateo et al. |
| 2018/0185461 A1 | 7/2018 | Vincendeau et al. |
| 2019/0351035 A1* | 11/2019 | Baeremaecker ..... C12N 9/2402 |

FOREIGN PATENT DOCUMENTS

| WO | WO 2016/185135 A1 | 11/2016 |
|---|---|---|
| WO | WO 2017/187179 A1 | 11/2017 |
| WO | WO 2020/144464 A1 | 7/2020 |
| WO | WO 2020/144465 A1 | 7/2020 |

OTHER PUBLICATIONS

Jackson et al. 2012 (Antigenic diversity is generated by distinct evolutionary mechanisms in African *trypanosome* species; PNAS 109(9):3416-3421) (Year: 2012).*
Black and Mansfield "Prospects for vaccination against pathogenic African trypanosomes", Parasite Immunol., vol. 38, No. 12, pp. 735-743 (2016).
Database Uniprot (Online), Protein—Uncharacterized Protein, gene -YVY486_0003730, Organism—Trypanosoma vivax (strain Y486), Database accession No. UniProt:F9WUZ3, Last modified Oct. 19, 2011.
Fleming et al., "Proteomic Identification of Immunodiagnostic Antigens for Trypanosoma vivax Infections in Cattle and Generation of a Proof-of-Concept Lateral Flow Test Diagnostic Device", PLoS Negl. Trop. Dis., vol. 10, No. 9, Article e0004977, 11 pages (2016).
GenBank Accession No. CCD21393.1, "Hypothetical protein, conserved in T. vivax [Trypanosoma vivax Y486]" NCBI, 1 page, Aug. 8, 2011.
Greif et al., "Transcriptome analysis of the bloodstream stage from the parasite Trypanosoma vivax", BMC Genomics, vol. 14, No. 149, 17 pages (2013).
Guedes et al., "A comparative in silico linear B-cell epitope prediction and characterization for South American and African Trypanosoma vivax strains", Genomics, vol. 111, No. 3, pp. 407-417 (2019).
International Search Report from International Application No. PCT/GB2020/050022, 6 pages, ISR Mailed May 14, 2020, application now published as International Publication No. WO2020/144464, published on Jul. 16, 2020.
International Search Report from International Patent Application No. PCT/GB2020/050023, 4 pages, mailed Mar. 20, 2020, application now published as International Publlication No. WO2020/144465 on Jul. 16, 2020.
Jackson et al., "Antigenic diversity is generated by distinct evolutionary mechanisms in African *trypanosome* species", Proc. Natl. Acad. Sci. U.S.A. vol. 109, No. 9, pp. 3416-3421 (2012).
Jackson et al., "Global Gene Expression Profiling through the Complete Life Cycle of Trypanosoma vivax", PLoS Neglected Tropical diseases, vol. 9, No. 8, J. e0003975, 29 pages (2015).
Li et al., "Immunization with recombinant beta-tubulin from Trypanosoma evansi induced protection against T. evansi, T. equiperdum and T. b. brucei infection in mice", Parasite Immunol., vol. 29, No. 4, pp. 191-199 (2007).
UniParc, "UPI000218C98C", UniProt, Organism: Trypanosoma vivax (strain Y486), Sequence UPI000218C98C, First Seen Oct. 19, 2011.
Ziegelbauer and Overath, "Organization of two invariant surface glycoproteins in the surface coat of Trypanosoma brucei", Infect. Immun., vol. 61, No. 11, pp. 4540-4545 (1993).

* cited by examiner

*Primary Examiner* — Mary Maille Lyons
(74) *Attorney, Agent, or Firm* — McDermott Will & Emery LLP; Judy Mohr; Peter Brunovskis (57) ABSTRACT

The invention relates to a trypanosomal vaccine, to pharmaceutical compositions comprising said vaccine and to their uses in vaccination to prevent trypanosomal infection in a mammal.

19 Claims, 9 Drawing Sheets

Specification includes a Sequence Listing.

FIGURE 2 (ctd)

FIGURE 2 (ctd)

FIGURE 3

FIGURE 3 (ctd)

FIGURE 4 (ctd)

FIGURE 4 (ctd)

TRYPANOSOMAL VACCINE

CROSS-REFERENCE TO RELATED APPLICATIONS

This application is a U.S. National Stage Application under 35 U.S.C. § 371 which claims the benefit of priority to International Patent Application No. PCT/GB2020/050022, filed Jan. 7, 2020, which claims the benefit of priority to GB Patent Application No. 1900187.4 filed Jan. 7, 2019, each of which is hereby incorporated by reference in its entirety.

FIELD OF THE INVENTION

The invention relates to a trypanosomal vaccine, to pharmaceutical compositions comprising said vaccine and to their uses in vaccination to prevent trypanosomal infection in a mammal.

BACKGROUND OF THE INVENTION

The livelihoods of millions of people living in Africa are at risk due to infectious diseases that affect the health of livestock animals that provide them with essential food, milk, clothing and draught power. One major livestock disease is animal African trypanosomiasis (AAT) which is caused by blood-dwelling Trypanosome parasites that affect many important farm animals including cattle, goats, sheep, horses, and pigs. AAT is endemic from the Southern edge of the Sahara to Zimbabwe/Mozambique and is estimated to cause annual productivity losses of over $1 billion, representing a major barrier for the socioeconomic advancement of many African countries. Such is the impact of this disease that the United Nations Food and Agricultural Organisation consider it to "lie at the heart of Africa's struggle against poverty".

The disease is mainly caused by two species of trypanosome: *T. congolense* and *T. vivax* which are transmitted through the bite of an infected tsetse fly. *T. vivax* transmission does not require tsetse flies for transmission and can be transmitted by other biting insects; as a consequence, *T. vivax* is a problem in countries outside of Africa, primarily Brazil. The few drugs available for AAT are not satisfactory: they cause serious side effects, and parasite resistance to these drugs is increasing. Importantly, even if new effective drugs were developed, these trypanosome parasites are endemic in wild animals meaning there would be little chance of eradicating the disease, and so livestock animals would require constant monitoring and treatment. The best solution would be the deployment of an effective vaccine; however, vaccinating against trypanosome infections has long been considered unachievable because the surface of these parasites is immunologically protected by a highly abundant cell surface protein called the variable surface glycoprotein (VSG). VSGs comprise a large family of related but not identical proteins, and trypanosomes express a small number or even a single variant on their surface at any one time. Host antibodies to VSG alleles are able to kill parasites; however, individual parasites within a population of trypanosomes can switch between variants and those that have switched to an antigenically distinct variant are able to effectively evade the host immune response ensuring the survival of the population as a whole.

One commonly-used strategy in the development of vaccines is to use inactivated or attenuated parasites, however, these vaccines are difficult to manufacture and can sometimes cause outbreaks if not appropriately attenuated. Modern vaccines, therefore, are typically purified recombinant proteins that can elicit protective immune responses and are consequently chemically defined.

There is therefore a great need to provide an alternative and effective vaccine against trypanosomes such as *T. vivax*.

SUMMARY OF THE INVENTION

According to a first aspect of the invention, there is provided a trypanosomal vaccine comprising a protein which comprises the amino acid sequence as set forth in SEQ ID NO: 1, or a protein having at least 90% sequence identity to said amino acid sequence, or a fragment of said amino acid sequence thereof, or a nucleic acid molecule encoding said protein.

According to a further aspect of the invention, there is provided a pharmaceutical composition comprising a trypanosomal vaccine as defined herein.

According to a further aspect of the invention, there is provided a method of preventing trypanosomal infection in a mammal which comprises administering to the mammal a therapeutically effective amount of the vaccine composition as defined herein.

According to a further aspect of the invention, there is provided a method of inducing an immune response in a mammal, wherein the method includes administering to the mammal, an effective amount of the vaccine composition as defined herein.

According to a further aspect of the invention, there is provided a kit of parts comprising a vaccine composition as defined herein, a medical instrument or other means for administering the vaccine composition and instructions for use.

BRIEF DESCRIPTION OF THE FIGURES

FIG. 2: Vaccination with the ectodomains of TvY486_0003730 confer protection in a murine model of *T. vivax* infection. (A) Five animals were vaccinated with TvY486_0003730 (solid line, filled squares) show attenuated *T. vivax* parasitaemia relative to adjuvant-only control animals (dotted lines, open circles). Parasitaemia was quantified in each animal by bioluminescence using the firefly luciferase gene transgenically expressed by the *T. vivax* strain used and plotted as a function of time post-infection. Survival curves indicate when animals were withdrawn from the study. (B) Comparisons of the parasitaemia on the indicated days post-infection in the vaccinated and control animals. Data points represent individual animals and horizontal bar represents mean±s.d. Comparisons were made using an one-way ANOVA with Dunnett's multiple comparison test for statistical confidence where * $P \leq 0.0001$; ** $P \leq 0.00001$. (C) Exemplar bioluminescence images of three control animals (numbers 1 to 3) and three vaccinated (numbers 4 to 6) on the indicated days post-infection. A cross indicates that the animal was removed from the study.

FIG. 3: Repeat vaccinations with an independent preparation of TvY486_0003730 in a larger cohort conforms vaccine effect in a murine model of *T. vivax* infection. (A) Fifteen animals were vaccinated with TvY486_0003730 (solid line filled squares) show attenuated *T. vivax* parasitaemia relative to adjuvant-only control animals (dotted lines open circles). Parasitaemia was quantified in each animal by bioluminescence using the firefly luciferase gene transgenically expressed by the *T. vivax* strain used and plotted as a function of time post-infection. Survival curves indicate when animals were withdrawn from the study. (B) Comparisons of the parasitaemia on the indicated days post-infection in the vaccinated and control animals. Data points represent individual animals and horizontal bear represents mean±s.d. Comparisons were made using the student t-test where statistical confidence is indicated as **** P≤0.00001.

FIG. 4: TvY486_0003730 induces protection from a *T. vivax* infection when used in the context of a vaccine. a, Cohorts of mice vaccinated with the indicated proteins were challenged with luciferase-expressing *T. vivax* parasites and bioluminescence measured on days 5 to 10 following challenge. Adjuvant-only controls are labelled as "Control". V31 elicited a longer delay to the ascending phase of parasitaemia and is highlighted with a box. y axis is Bioluminescence (ph/s) and x axis is Time post-challenge (days). b, Bioluminescent imaging of adjuvant-only control and mice vaccinated with V31 six and eight days after challenge with *T. vivax*. c, Quantification of repeat bioluminescent *T. vivax* infections in larger cohorts of 15 mice with V31 showing protective effects in the initial screen. Bars indicate mean±SD, ns=not significant, **** P≤0.00001 student t-test.

DETAILED DESCRIPTION OF THE INVENTION

According to a first aspect of the invention, there is provided a trypanosomal vaccine comprising a protein which comprises the amino acid sequence as set forth in SEQ ID NO: 1, or a protein having at least 90% sequence identity to said amino acid sequence, or a fragment of said amino acid sequence thereof, or a nucleic acid molecule encoding said protein.

The present invention relates to the identification of non-variant cell surface *T. vivax* proteins, which, when used in the context of a vaccine can elicit protective immune responses. Using the genome sequence to identify potential candidates, a vaccine target antigen has been identified which, when produced as a purified recombinant protein and administered with an appropriate immunostimulatory adjuvant, confers protection to *T. vivax* infections in mice. The results presented herein indicate that this non-variant parasite protein will be an important component of a vaccine to prevent AAT in livestock animals.

References herein to the amino acid sequence set forth in SEQ ID NO: 1 refer to:

(SEQ ID NO: 1)
IDDEGESAQFRTWVCKWEQKRTVLLYYIRVLIAKTARDAGALRQQRAAF

FEAWSNAVSLRNLKNVAKKVKKATEAVDWATQCEGVMFMTLQTIIRALN

TMRGHVSDKDGTAPSDCGLEPHQGRAADRNMTYVEVIEHIKSTERRLQE

LSMFAEESVRTFYGNYVNGVGLLNDTNNYFAAAEAARRALREADEAMKD

-continued
ASDRKELNEKRVQLGCEVEKGLFFMREIFLTLHSVSERVISRERALKAK

VGELDEGPGACGMAHTMFRSTAYANLRASSAKDESSLAVVELSEFMGIK

GHSTLHHELEYDDDFKISLTNCRDSELEQSLVFRFARGEENDNIYDFDR

WRAAADELWNKVESHTHIISEKCTKVSGVDCSEAVGAVTMLIGRLRQLE

GDLERGLGAAIRALKTVEDGIATSQDAMRKCQHGGAVNEHHTEAKEPQT

TSGRREANTDSAPAKEQLDAASKLEGGSRLEEEVDGNEKEEQQEAPANG

PQGALGVRQEETSYEGDAGRGSVDTGHDEFATYLASRSACSTAGDGIES

SSTAGDAAAVEARS.

The amino acid sequence of SEQ ID NO: 1 corresponds to the ectodomain of a cell surface *T. vivax* protein known as TvY486_0003730.

The full length amino acid sequence of TvY486_0003730 is shown below:

(SEQ ID NO: 2)
MLAYKLILCSTVFLLCPIVAFSIDDEGESAQFRTWVCKWEQKRTVLLYY

IRVLIAKTARDAGALRQQRAAFFEAWSNAVSLRNLKNVAKKVKKATEAV

DWATQCEGVMFMTLQTIIRALNTMRGHVSDKDGTAPSDCGLEPHQGRAA

DRNMTYVEVIEHIKSTERRLQELSMFAEESVRTFYGNYVNGVGLLNDTN

NYFAAAEAARRALREADEAMKDASDRKELNEKRVQLGCEVEKGLFFMRE

IFLTLHSVSERVISRERALKAKVGELDEGPGACGMAHTMFRSTAYANLR

ASSAKDESSLAVVELSEFMGIKGHSTLHHELEYDDDFKISLTNCRDSEL

EQSLVFRFARGEENDNIYDFDRWRAAADELWNKVESHTHIISEKCTKVS

GVDCSEAVGAVTMLIGRLRQLEGDLERGLGAAIRALKTVEDGIATSQDA

MRKCQHGGAVNEHHTEAKEPQTTSGRREANTDSAPAKEQLDAASKLEGG

SRLEEEVDGNEKEEQQEAPANGPQGALGVRQEETSYEGDAGRGSVDTGH

DEFATYLASRSACSTAGDGIESSSTAGDAAAVEARSKKKYLALMSVLCF

LFVSAASVVLLAWKRTKL wherein the underlined portion represents the ectodomain region of TvY486_0003730.

TvY486_0003730 is also referred to herein as V31. Data is presented herein which surprisingly shows that V31 elicited a longer delay to the ascending phase of parasitaemia. In a repeat study, V31 further reduced the rate of parasite multiplication (see Study 2 and FIG. 4). This coupled with the remaining data presented herein from both Study 1 and Study 2 indicate that V31 represents a promising candidate for *T. vivax* infection.

In one embodiment, the trypanosomal vaccine as defined herein comprises a protein which comprises the amino acid sequence as set forth in SEQ ID NO: 1, or a protein having at least 90% sequence identity to said amino acid sequence, or a fragment of said amino acid sequence thereof.

It will be appreciated that references herein to "identity" are to be understood as meaning the percentage identity between two protein sequences, e.g.: SEQ ID NO: X and SEQ ID NO: 1, which is the sum of the common amino acids between aligned sequences SEQ ID NO: X and SEQ ID NO: 1, divided by the shorter length of either SEQ ID NO: X or SEQ ID NO: 1, expressed as a percentage.

In one embodiment, the protein of the invention has greater than 90% sequence identity with the ectodomain region of TvY486_0003730 (SEQ ID NO: 1), such as at least 91%, 92%, 93%, 94%, 95%, 96%, 97%, 98% or 99% sequence identity with the ectodomain region of TvY486_0003730 (SEQ ID NO: 1).

References herein to 'fragment' include, for example, functional fragments with a C-terminal truncation, or with an N-terminal truncation. Fragments are suitably greater than 10 amino acids in length, for example greater than 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 amino acids in length.

In a further embodiment, the protein of the invention consists of the amino acid sequence as set forth in SEQ ID NO: 1.

In an alternative embodiment, the vaccine comprises a nucleic acid molecule encoding said protein of the invention. References herein to "nucleic acid molecule" typically refers to DNA or RNA. In a further embodiment, the nucleic acid molecule comprises an oligonucleotide encoding said protein.

References herein to "trypanosomal" refer to a genus of kinetoplastids (class Kinetoplastida), a monophyletic group of unicellular parasitic flagellate protozoa. The name is derived from the Greek trypano-(borer) and soma (body) because of their corkscrew-like motion. Most trypanosomes are heteroxenous (requiring more than one obligatory host to complete life cycle) and most are transmitted via a vector. The majority of species are transmitted by blood-feeding invertebrates, but there are different mechanisms among the varying species. Some, such as *Trypanosoma equiperdum*, are spread by direct contact. In an invertebrate host they are generally found in the intestine, but normally occupy the bloodstream or an intracellular environment in the mammalian host.

Examples of trypanosomal species include: *T. ambystomae, T. antiquus, T. avium, T. boissoni, T. brucei, T. cruzi, T. congolense, T. equinum, T. equiperdum, T. evansi, T. everetti, T. hosei, T. irwini, T. lewisi, T. melophagium, T. paddae, T. parroti, T. percae, T. rangeli, T. rotatorium, T. rugosae, T. sergenti, T. simiae, T. sinipercae, T. suis, T. theileri, T. triglae, T. tungarae* and *T. vivax*.

In one embodiment, the trypanosomal vaccine is a *T. congolense* or *T. vivax* vaccine. In a further embodiment, the trypanosomal vaccine is a *T. vivax* vaccine.

According to a further aspect of the invention, there is provided a pharmaceutical composition comprising a trypanosomal vaccine as defined herein.

In one embodiment, the vaccine composition additionally comprises one or more adjuvants. References herein to the term "adjuvant" refer to a compound that, when used in combination with a specific immunogen in a formulation, will augment or otherwise alter or modify the resultant immune response. Modification of the immune response can include intensification or broadening the specificity of either or both antibody and cellular immune responses. Modification of the immune response can also mean decreasing or suppressing certain antigen-specific immune responses.

In a further embodiment, at least about 1 μg and up to about 20 μg adjuvant is present within the vaccine composition. Examples of suitable adjuvants include: alum; aluminum hydroxide; aluminum phosphate; calcium phosphate hydroxide; paraffin oil; killed bacteria such as *Bordetella pertussis, Mycobacterium bovis* and toxoids; squalene, detergents; plant saponins from quillaja, soybean, polygala senega; cytokines such as IL-1, IL-2, IL-12; Freund's complete adjuvant; and Freund's incomplete adjuvant.

In a yet further embodiment, said adjuvant comprises aluminium hydroxide, such as a wet gel suspension of aluminium hydroxide, in particular Alhydrogel®, more particularly Alhydrogel® 2%. In one particular embodiment, said adjuvant comprises Montanide® ISA 201 VG. This adjuvant is a water-in-oil-in-water adjuvant and full details of this adjuvant may be found: https://www.seppic.com/montanide-isa-w-o-w. In an alternative embodiment, said adjuvant comprises Quil-A®. Quil-A® adjuvant is a saponin adjuvant which is used in a wide variety of veterinary vaccines. Full details of Quil-A® may be found: https://www.invivogen.com/quila.

In one embodiment, the vaccine composition additionally comprises a pharmaceutically acceptable carrier, diluent, excipient, or combination thereof, in which the immunogen (i.e. the proteins as defined herein) is/are suspended or dissolved.

Pharmaceutically acceptable carriers are known, and include but are not limited to, water for injection, saline solution, buffered saline, dextrose, water, glycerol, sterile isotonic aqueous buffer, and combinations thereof. For parenteral administration, such as subcutaneous injection, the carrier may include water, saline, alcohol, a fat, a wax, a buffer or combinations thereof. Pharmaceutically acceptable carriers, diluents, and other excipients are described in detail in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

In other embodiments, the vaccine composition can include one or more diluents, preservatives, solubilizers and/or emulsifiers. For example, the vaccine composition can include minor amounts of wetting or emulsifying agents, or pH buffering agents to improve vaccine efficacy. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

It may also be desirable to include other components in a vaccine composition, such as delivery vehicles including but not limited to aluminum salts, water-in-oil emulsions, biodegradable oil vehicles, oil-in-water emulsions, biodegradable microcapsules, and liposomes. In other embodiments, the vaccine composition can include antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Administration of the vaccine composition can be systemic or local. Methods of administering a vaccine composition include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions described herein are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition may induce an antibody or other immune response that is substantially higher than other routes of administration. In another embodiment, intranasal or other mucosal routes of administration of a composition described herein may induce an antibody or other immune response at the site of immunization.

In one embodiment, the vaccine composition has a volume of between about 50 µl and about 500 µl.

According to a further aspect of the invention, there is provided a method of preventing trypanosomal infection in a mammal which comprises administering to the mammal a therapeutically effective amount of the vaccine composition as defined herein.

References herein to "trypanosomal infection" refer to infection by a trypanosome as defined herein, such as *T. congolense* or *T. vivax*, in particular *T. vivax*. Thus, in one embodiment, the trypanosomal infection is an infection mediated by *Trypanosoma vivax*.

In one embodiment, the trypanosomal infection is animal African trypanosomiasis (AAT). References herein to "effective amount" refer to a dose which is sufficient or most likely to elicit antibodies such that the immunized subject has reduced severity of infection.

According to a further aspect of the invention, there is provided a method of inducing an immune response in a mammal, wherein the method includes administering to the mammal, an effective amount of the vaccine composition as defined herein.

Examples of suitable mammals include ungulates, such as those selected from cattle, goats, sheep, horses, pigs and camels.

In one embodiment, the vaccine composition is administered in a single dose regimen. In another embodiment, the vaccine composition is administered in a two dose regimen that includes a first and a second dose. In one embodiment, the second dose is administered at least about 1 week, 2 weeks, 3 weeks, 1 month or 1 year after the first dose. In another embodiment, the vaccine composition is administered in a three dose regimen.

According to a further aspect of the invention, there is provided a kit of parts comprising a vaccine composition as defined herein, a medical instrument or other means for administering the vaccine composition and instructions for use.

In one embodiment, the vaccine composition is packaged in a hermetically sealed container such as an ampoule or sachette indicating the quantity of composition. In one embodiment, the composition is supplied as a liquid. In another embodiment, the composition is supplied as a dry sterilized lyophilized powder or water free concentrate in a hermetically sealed container, wherein the composition can be reconstituted, for example, with water or saline, to obtain an appropriate concentration for administration to a subject.

When the vaccine composition is systemically administered, for example, by subcutaneous or intramuscular injection, a needle and syringe, or a needle-less injection device can be used. The vaccine formulation can be enclosed in ampoules, disposable syringes or multiple dose vials made of glass or plastic.

The following studies illustrate the invention:

Study 1

Materials and Methods

Design, Synthesis and Purification of *T. vivax* TvY486_0003730

The region corresponding to the entire extracellular domains of TvY486_0003730 was determined by using transmembrane (TMHMMv2.0 (Sonnhammer et al. (1998) Proceedings International Conference on Intelligent Systems for Molecular Biology 6, 175-182) and signal peptide prediction software (SignalP v4.0 (Petersen et al. (2011) Nature methods 8, 785-786)). Sequences encoding the entire extracellular domains of these proteins from the Y486 strain of *Trypanosoma vivax*, with the exception of their signal peptide, were made by gene synthesis (GeneartAG, Germany and Twist Bioscience, USA). All sequences were codon-optimized for expression in human cells. The coding sequences were flanked by unique NotI and AscI sites and cloned into a derivative of the pTT3 expression vector between the leader sequence of the mouse variable light chain 7-33 (Crosnier et al. (2013) Molecular & cellular proteomics: MCP 12, 3976-3986). The ectodomain was expressed as a soluble recombinant protein in HEK293 cells as described (Crosnier et al. (2013), supra). Protein was purified by Ni2+ immobilised metal ion affinity chromatography using HisTRAP columns (GEHealthcare, UK), eluted in 400 mM imidazole as described (Bartholdson et al. (2012) PLoS pathogens 8, e1003031), dialysed into HBS, aliquoted and snap-frozen prior to immunisation.

Animals, Immunisations, Challenge and Bioluminescence Measurement

All animal experiments were performed in accordance with UK Home office legislation and according to local ethical review board approval. Six to eight-week old female BALB/c mice were bred and housed at the Research Support Facility of the Wellcome Trust Sanger Institute. Recombinant proteins were adsorbed to Alhydrogel® adjuvant 2% (Brenntag Biosector, Denmark) as an adjuvant using a final volume ratio of 1:1. Animals were immunised intraperitoneally with an initial priming dose of 100 micrograms followed by two further booster immunisations of 100 micrograms given at two week intervals.

Vaccinated animals were rested for 4 weeks after the final immunisation to mitigate any possible non-specific protective effects elicited by residual adjuvant. Animal challenges were performed using a transgenic form of the *T. vivax* Y486 strain genetically engineered to ubiquitously express the firefly luciferase enzyme as described (Chamond et al. (2010) PLoS neglected tropical diseases 4, e792). Parasites were maintained by weekly passage in wild type BALB/c mice. For infection challenges, bloodstream forms of *T. vivax* parasites were obtained from the blood of an infected donor mouse at the peak of parasitaemia and between 100 to 1000 parasites were used to infect mice by intravenous injection.

From day three post-infection, animals were injected intraperitoneally with luciferase substrate, D-luciferin (D-Luciferin potassium salt, Source BioScience, Nottingham, UK) at a dose of 200 mg/kg, 10 mins before bioluminescence acquisitions. The mice were anaesthetized with 3% isoflurane and placed in the imaging chamber for analysis. Emitted photons were acquired by a charge coupled device (CCD) camera (IVIS Spectrum Imaging System, Perkin Elmer). Total photons emitted from the image of each mouse were quantified using Living Image software (Xenogen Corporation, Almeda, California), and results were expressed as number of photons/sec/ROI. Seven days post-challenge, thin-film parasitemia quantification was conducted where blood parasite counts were established under a light microscope and expressed as the number of parasites per milliliter of blood as an independent measurement of parasite load.

Results

To discover potential subunit vaccine candidates for *T. vivax*, we analysed the genome sequence to identify proteins that fulfilled the following criteria: 1) were predicted to encode cell surface proteins that would be accessible to vaccine-elicited host antibodies; 2) did not belong to a paralogous group of parasite proteins that might indicate functional redundancy; 3) contained more than 300 amino acids and so are likely to project beyond the VSG coat on the parasite membrane. A protein that met these criteria was TvY486_0003730.

Figure 1:
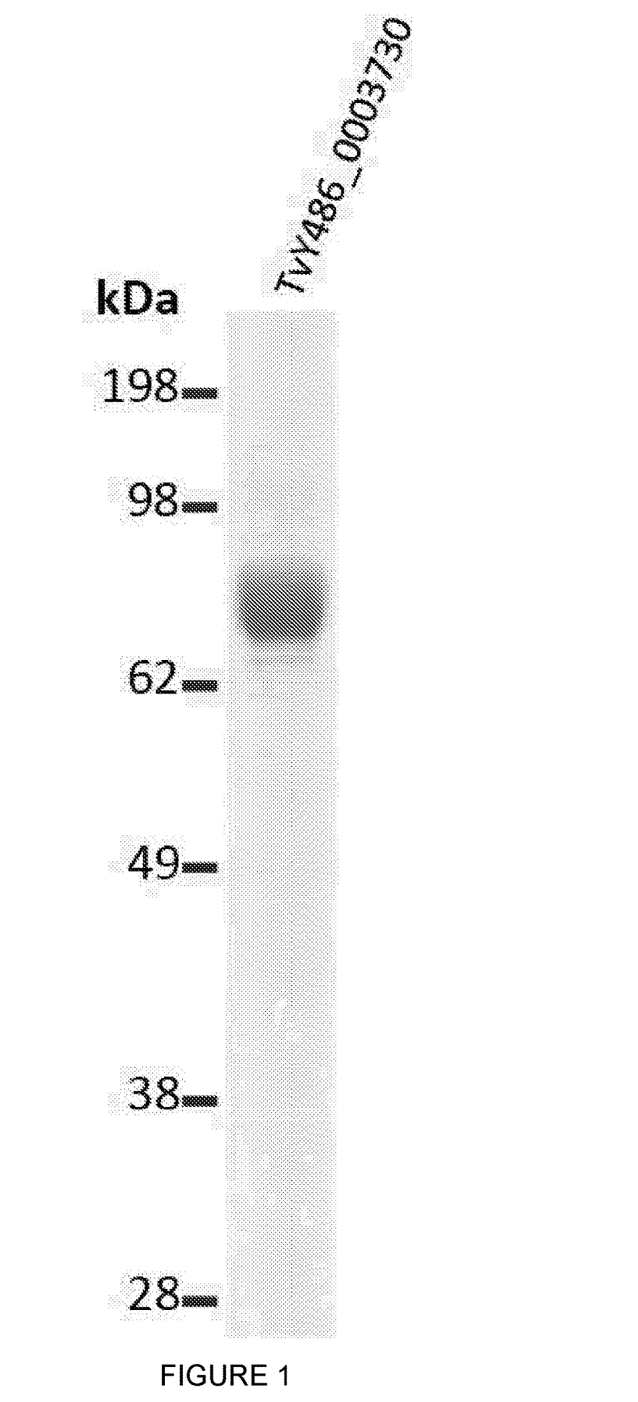
FIG. 1: Expression and purification of the extracellular regions of TvY486_0003730. Protein consisting of the entire ectodomain was expressed as a soluble recombinant protein in HEK293 cells and purified from spent tissue culture media using immobilised metal ion chromatography. Approximately one microgram of purified protein was resolved by SDS-PAGE under reducing conditions. The protein migrated as a series of glycoforms around the expected mass.
Figure 2:
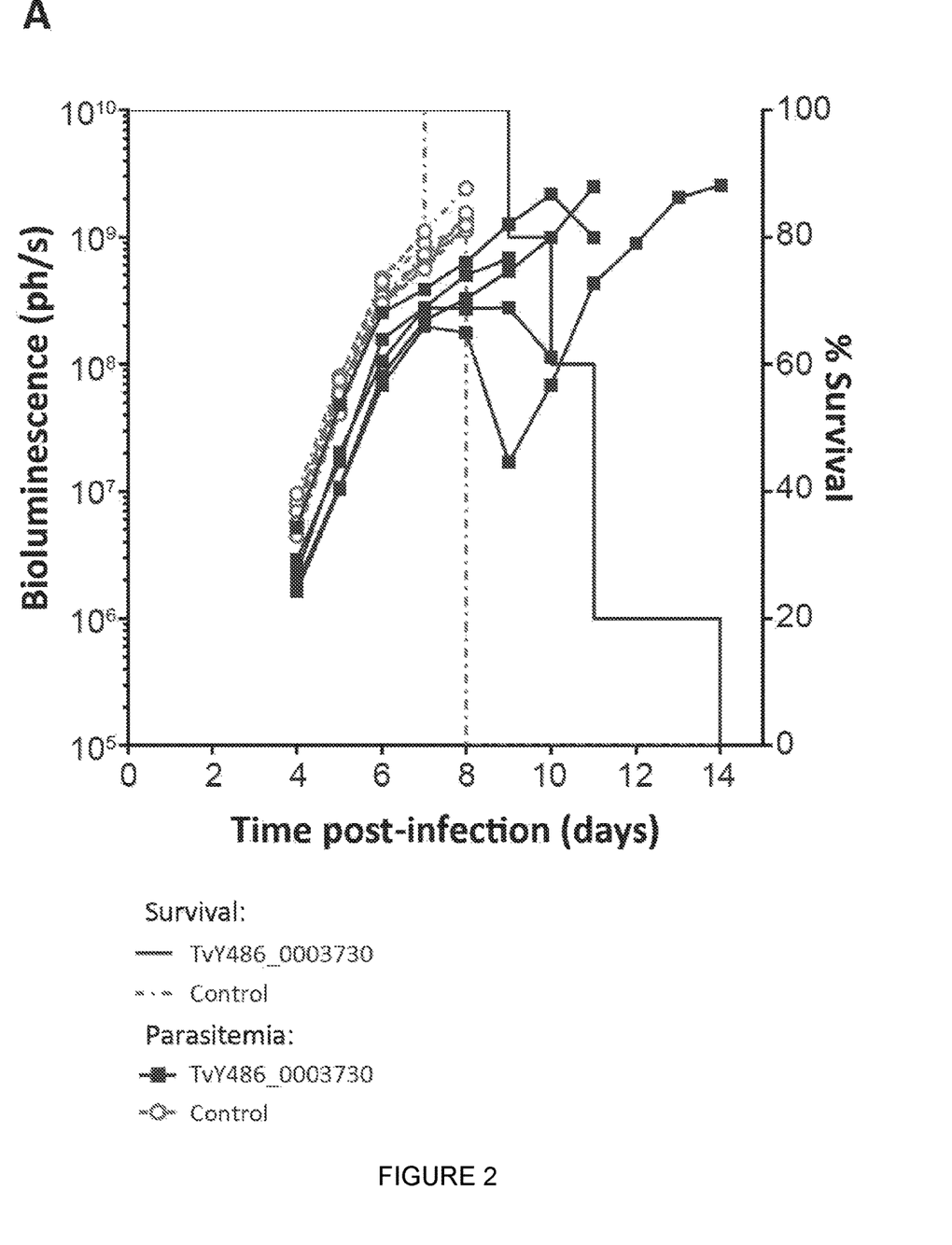
Figure 3:
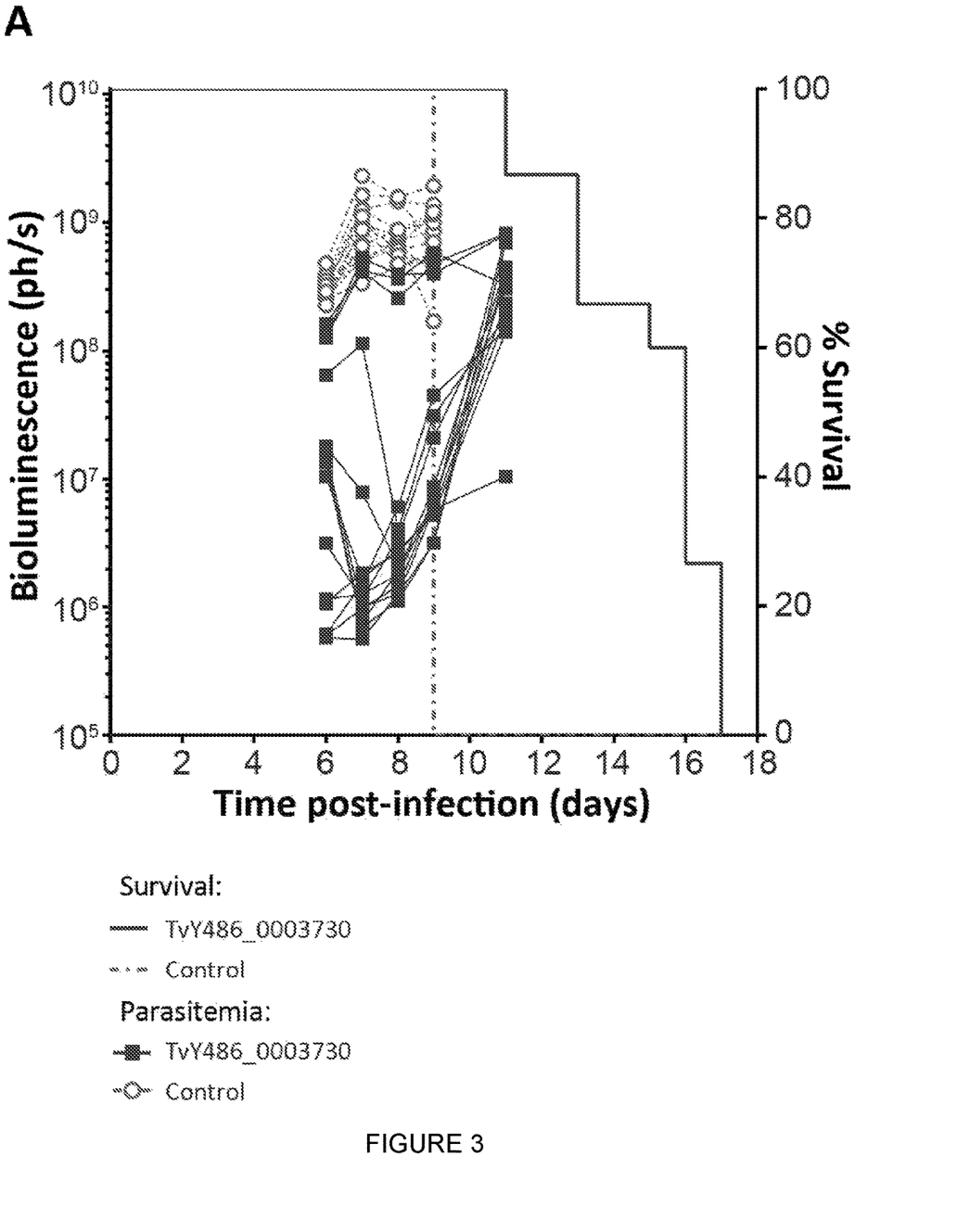

To increase the chances that the extracellular regions of the protein were expressed in a correctly folded conformation and therefore elicit antibodies that would bind to the native parasite protein, we expressed the protein using a mammalian expression system to promote the formation of structurally-critical disulphide bonds. The entire ectodomain region was identified and the gene constructed by gene synthesis using codons optimised for expression in human cells. This gene construct was cloned into a mammalian protein expression plasmid. Human embryonic kidney (HEK)293 cells were transfected with this plasmid and the protein secreted into the tissue culture medium. The protein was purified from the tissue culture supernatant by immobilised metal ion chromatography (IMAC) and resolved as a series of glycoforms by SDS-PAGE (FIG. 1).

Groups of five mice were immunised intraperitoneally using a prime followed by two boost regime with the protein adjuvanted with Alhydrogel; control animals were immunised with adjuvant only. Vaccinated animals were challenged with *T. vivax* parasites delivered intravenously from the blood of an infected donor animal. Animals immunised with TvY486_0003730 exhibited significant delays in parasitaemia relative to adjuvant-only control mice (FIGS. 2A, B and C). To confirm these results, a larger cohort of 15 animals were immunised with an independent preparation of TvY486_0003730 and again most vaccinated animals showed evidence of protection (FIGS. 3A and B).

Study 2

Materials and Methods

Mouse Strains and Ethical Approvals

All animal experiments were performed under UK Home Office governmental regulations (project license number PD3DA8D1F) and European directive 2010/63/EU. Research was ethically approved by the Sanger Institute Animal Welfare and Ethical Review Board. Mice were obtained from the Research Support Facility, Wellcome Sanger Institute.

*Trypanosoma vivax* Parasite Strain and Maintenance

A transgenic form of *Trypanosoma vivax* genetically engineered to ubiquitously express the firefly luciferase enzyme was kindly provided by the Institut Pasteur, Paris. The parental strain of this parasite is the IL1392 line derived from the Y486 strain used for genome sequencing (Jackson et al. 2012, Proc. Natl. Acad. Sci. U.S.A. 109, 3416-3421) and is fully documented by Chamond et al. (Chamond et al. 2010, PLoS Negl. Trop. Dis. 4, e792). Parasites were initially recovered from a frozen sample by intraperitoneal administration into two mice and transferred to naïve mice when parasites became patent in the blood. Parasites were maintained by weekly serial blood passage in wild type female BALB/C mice by taking a blood biopsy, quantifying living parasites in PBS/10 mM D-glucose by microscopy and infecting four naïve mice by intravenous infection. During the course of the project, two further aliquots of frozen parasites were thawed and then used for infection challenges, no significant differences in the kinetics of infection between the batches of parasites were observed.

Quantification of *Trypanosoma vivax* Infections by Bioluminescent In Vivo Imaging To quantify *T. vivax* infections by bioluminescent in vivo imaging, infected animals were intraperitoneally administered with the luciferase substrate, luciferin. D-luciferin (potassium salt, Source BioScience, UK) was reconstituted to 30 mg $mL^{-1}$ in Dulbecco's PBS without $Ca^{2+}$ and $Mg^{2+}$ (Hyclone), filter-sterilised (0.22 μm) and stored in aliquots at −20° C. Aliquots were thawed and administered to animals at a dose of 200 mg/kg, by intraperitoneal injection ten minutes before bioluminescence acquisitions. The mice were given three minutes of free movement before being anaesthetized with 3% isoflurane and placed in the imaging chamber where anaesthesia was maintained for acquisition. To determine the long-term persistence of the parasites in different organs of infected mice, animals were administered with luciferin, imaged, and then euthanised with an overdose of anaesthetic. Mice were then perfused with PBS until the perfusion fluid ran clear, the organs dissected, arranged on a petri dish, and bathed in PBS containing 10 mM glucose and luciferin for imaging. Emitted photons were acquired by a charge coupled device (CCD) camera (IVIS Spectrum Imaging System, Perkin Elmer). Total photons emitted from the image of each mouse were quantified using Living Image software (Xenogen Corporation, Almeda, California), and the results were expressed as bioluminescence: number of photons/sec/ROI.

Vaccine Target Identification and Expression

The *T. vivax* genome was searched for proteins encoding predicted type I, GPI-anchored and secreted proteins using protein feature searching in TryTrypDB (Aslett et al. 2010, Nucleic Acids Res. 38, D457-D462). The regions corresponding to the entire extracellular domains of *T. vivax* cell-surface and secreted proteins from the Y486 strain were determined by using transmembrane (Sonnhammer et al. 1998, Proc. Int. Conf. Intell. Syst. Mol. Biol. 6, 175-182) and GPI-anchor (Eisenhaber et al. 1999, J. Mol. Biol. 292, 741-758) or signal peptide (Bendtsen et al. 2004, J. Mol. Biol. 340, 783-795) prediction software. Protein sequences encoding the extracellular domain and lacking their signal peptide, were codon-optimized for expression in human cells and made by gene synthesis (GeneartAG, Germany and Twist Bioscience, USA). The sequences were flanked by unique NotI and AscI restriction enzyme sites and cloned into a pTT3-based mammalian expression vector (Durocher et al. 2002, Nucleic Acids Res. 30, E9) between an N-terminal signal peptide to direct protein secretion and a C-terminal tag that included a protein sequence that could be enzymatically biotinylated by the BirA protein-biotin ligase (Bushell et al. 2008, Genome Res. 18, 622-630) and a 6-his tag for purification (Sun et al. 2012, Anal. Biochem. 424, 45-53). The ectodomain was expressed as a soluble recombinant protein in HEK293 cells which were obtained from Yves Durocher (NRC, Montreal) as described (Crosnier et al. 2013, Mol. Cell. Proteomics 12, 3976-3986; Kerr and Wright 2012, J. Vis. Exp. e3881). Cell lines were regularly tested (every six months, Surrey Diagnostics, UK) for *mycoplasma* contamination and found to be negative. To prepare purified proteins for immunisation, between 50 and 1.2 L (depending on the level at which the protein was expressed) of spent culture media containing the secreted ectodomain was harvested from transfected cells, filtered and purified by $Ni^{2+}$ immobilised metal ion affinity chromatography using HisTRAP columns using an AKTAPure instrument (GEHealthcare, UK). Proteins were eluted in 400 mM imidazole as described (Bartholdson et al. 2012, PLoS Pathog. 8, e1003031), and extensively dialysed into HBS before quantified by spectrophotometry at 280 nm. Protein purity was determined by resolving approximately one microgram of purified protein by SDS-PAGE using NuPAGE 4-12% Bis Tris precast gels (ThermoFisher) for 50 minutes at 200V. Where reducing conditions were required NuPAGE reducing agent and anti-oxidant (Invitrogen) were added to the sample and the running buffer, respectively. The gels were stained with SYPRO Orange (ThermoFisher), destained in 7.5% acetic acid and imaged using a Typhoon 9400 phosphoimager (GE Healthcare). Purified proteins were aliquoted and stored frozen at −20° C. until use. Where enzymatically monobiotinylated proteins were required to determine antibody titres by ELISA, proteins were co-transfected with a secreted version of the protein biotin ligase (BirA) as described (Kerr and Wright 2012, supra), and extensively dialysed against HEPES-buffered saline and their level of expression determined by ELISA.

Vaccine Formulation and Administration

For the initial screening of antigens, aliquots of purified protein for immunisation were thawed, diluted in PBS and mixed 50% v/v with Alhydrogel adjuvant 2% (InvivoGen) for two hours at room temperature. For each antigen, groups of five six to eight-week old female BALB/C mice were immunised intraperitoneally initially with 100 μg protein followed by two additional fortnightly immunisations using 20 μg protein. Where the quantity of purified antigen was insufficient to achieve these levels, lower doses of proteins were administered.

*Trypanosoma vivax* Vaccine Testing

For infection challenges, bloodstream forms of *T. vivax* parasites were obtained from the blood of an infected donor mouse at the peak of parasitaemia, diluted in PBS/10 mM D-glucose, quantified by microscopy, and between 100 to 1000 parasites were used to infect mice by intravenous injection. While establishing the infection model in our facility, we observed that the *T. vivax* parasite was labile and gradually lost virulence once removed from living mice. To reduce the possibility of any artefactual protective effects being due to the loss of parasite virulence during the challenge procedure, we screened the protective effects of antigens in a cohort design. Each cohort contained six cages of five animals: four cages contained mice immunised with a different query subunit vaccine candidate, and the other two cages contained control mice immunised with adjuvant alone. During the infection procedure, the mice in the control cages were challenged first and last and the data from the cohort only used if the infections in the control mice from the two cages were not statistically different. During the infection procedures, parasites were outside of a living mouse for no more than 30 minutes. Eight to ten days after the final immunisation, blood biopsies were collected from the tail of each animal and clotted for two hours at room temperature. Cells were removed by centrifugation and sera collected, sodium azide added to a final concentration of 2 mM and stored at −20° C. Vaccinated animals were rested for four weeks after the final immunisation to mitigate any possible non-specific protective effects elicited by residual adjuvant.

Mice were normally challenged by intravenous delivery of $10^2$ to $10^3$ parasites for the initial screening and passive transfer protection experiments, but were also challenged intraperitoneally during the establishment of the model and subcutaneously when investigating the duration of protection. For retesting antigens, two groups of 15 animals were each housed in three cages containing five mice. The animals were not randomised between cages and the operator was not blinded to the group condition. Groups were compared using bioluminescence quantification as a proxy for parasitaemia and groups were compared using one-way ANOVA. No readings were excluded from the analysis.

Results

Investigation of V31 Immunity to *T. vivax*

The gene sequence encoding the entire extracellular region of V31 was synthesised and cloned into a mammalian protein expression plasmid containing a secretion peptide and purification tags. V31 was expressed as a soluble recombinant protein in mammalian HEK293 cells to increase the chances that structurally-critical posttranslational modifications were added and therefore elicit host antibodies that recognize native antigens displayed by the parasite. V31 yielded sufficient protein after purification for the vaccination trials. For vaccination, we selected a prime and two boost regime using alum as an adjuvant to bias host responses towards humoral immunity. To reduce any systemic adjuvant-elicited effects on disease progression, vaccinated animals were rested for four weeks following the final boost before parasite challenge. In preliminary experiments, we observed that *T. vivax* lost virulence once removed from donor animals, and so to avoid confounding effects due to loss of parasite viability during the infection procedure, we ensured that infections were comparable in control animals challenged before and after animals vaccinated with the V31 antigen.

Figure 4:
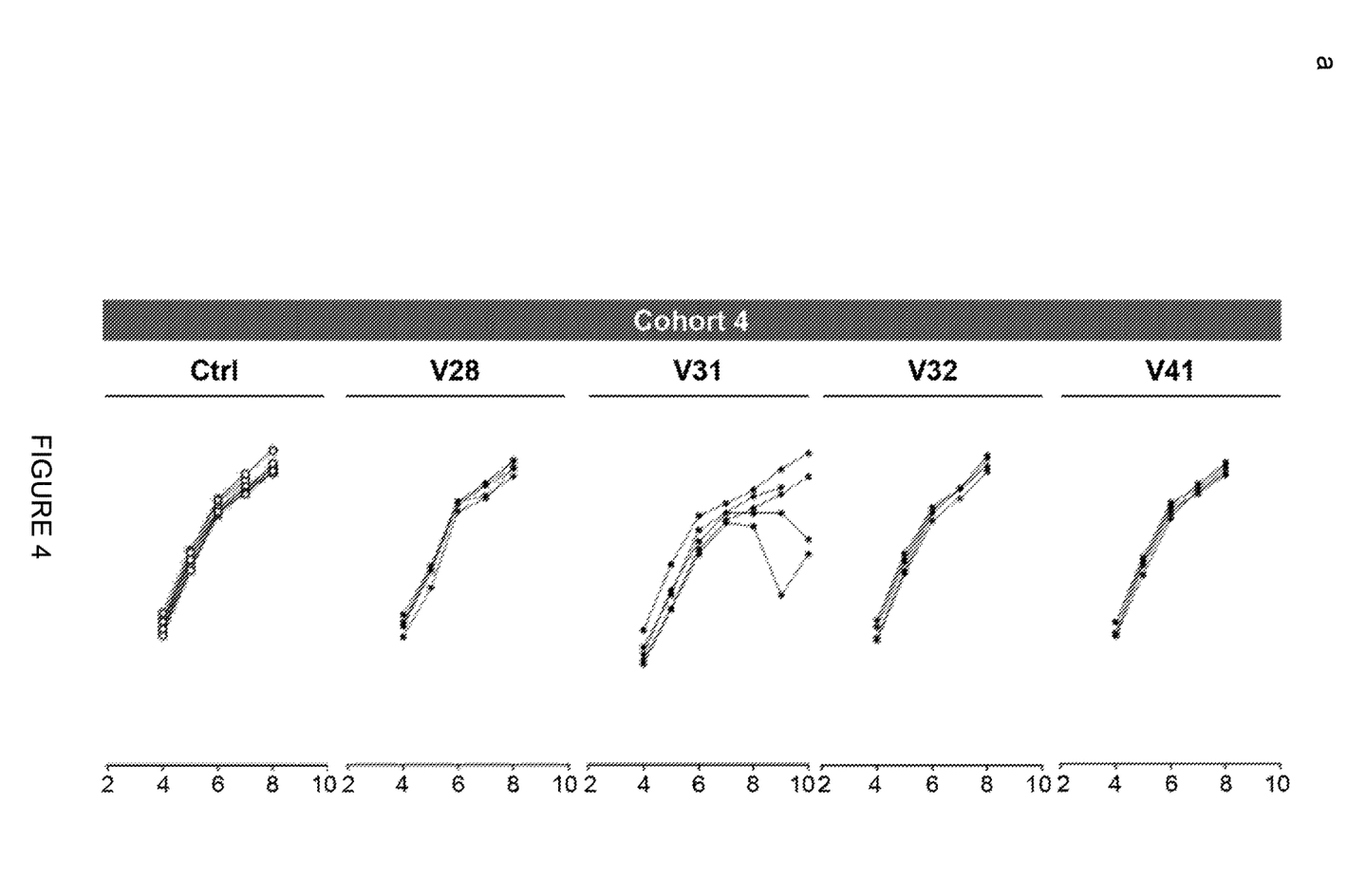

We observed that V31 exhibited a longer delay to the ascending phase of parasitaemia (FIG. 4a, b). Experiments were repeated using independent protein preparations and larger cohorts of animals. We observed that V31 reduced the rate of parasite multiplication (FIG. 1c). Dissection of protected animals following infection revealed no obvious extravascular reservoirs of parasites.

Discussion

Animal African trypanosomiasis continues to be a significant impediment in the successful raising of livestock animals in sub-Saharan Africa and previous attempts to vaccinate against the trypanosome parasites that cause this disease have been unsuccessful. Here we have shown that vaccinating with a recombinant protein comprising the entire ectodomain of a conserved *T. vivax* cell surface protein TvY486_0003730 confers protection in a mouse model of infection suggesting that this protein could be an effective subunit vaccine. We note that the disease is acute in the BALB/c mice used in our infection trials since control mice develop rapid uncontrolled parasitaemia whereas in livestock animals such as goats and cattle the infection is typically a chronic disease with lower parasitaemia suggesting the mouse infection model provides a stringent test of our vaccine candidates. We envisage that a vaccine containing TvY486_0003730 in whole or in part and in the context of an appropriate adjuvant will constitute a vaccine to treat this disease in livestock animals.

The invention claimed is:

1. A trypanosomal vaccine, comprising:
   a protein comprising an amino acid sequence set forth in SEQ ID NO: 1; and
   one or more adjuvants.

2. The trypanosomal vaccine of claim 1, which is a *Trypanosoma vivax* vaccine.

3. The trypanosomal vaccine of claim 1, wherein said one or more adjuvants comprise a mineral oil water-in-oil-in-water adjuvant.

4. The trypanosomal vaccine of claim 1, which additionally comprises a pharmaceutically acceptable carrier, diluent, excipient, or combination thereof.

5. A method of vaccinating against a trypanosomal infection in a mammal, comprising: administering to the mammal a therapeutically effective amount of the trypanosomal vaccine of claim 1.

6. The method of claim 5, wherein the trypanosomal infection is an infection mediated by *Trypanosoma vivax*.

7. The method of claim 5, wherein the trypanosomal infection is animal African trypanosomiasis (AAT).

8. A method of inducing an immune response in a mammal, wherein the method comprises administering to the mammal an effective amount of the trypanosomal vaccine of claim 1.

9. The method of claim 5, wherein the mammal is an ungulate.

10. A kit of parts, comprising: the trypanosomal vaccine of claim 1, a medical instrument or other means for administering the pharmaceutical composition and instructions for use.

11. The method of claim 9, wherein the ungulate is selected from the group consisting of cattle, goats, sheep, horses, pigs and camels.

12. The method of claim 5, wherein the trypanosomal vaccine is administered by parenteral administration.

13. The method of claim 12, wherein the trypanosomal vaccine is administered intradermally, intramuscularly, intravenously, or subcutaneously.

14. The method of claim 5, wherein the trypanosomal vaccine is administered by epidural or mucosal administration.

15. The method of claim 5, wherein the trypanosomal vaccine is administered by intranasal, oral, pulmonary or rectal administration.

16. The method of claim 8, wherein the trypanosomal vaccine is administered by parenteral administration.

17. The method of claim 16, wherein the trypanosomal vaccine is administered intradermally, intramuscularly, intravenously, or subcutaneously.

18. The method of claim 8, wherein the trypanosomal vaccine is administered by epidural or mucosal administration.

19. The method of claim 8, wherein the trypanosomal vaccine is administered by intranasal, oral, pulmonary or rectal administration.

* * * * *

SEQUENCE LISTING

<160> NUMBER OF SEQ ID NOS: 2

<210> SEQ ID NO 1
<211> LENGTH: 553
<212> TYPE: PRT
<213> ORGANISM: T. vivax

<400> SEQUENCE: 1

```
Ile Asp Asp Glu Gly Glu Ser Ala Gln Phe Arg Thr Trp Val Cys Lys
1               5                   10                  15

Trp Glu Gln Lys Arg Thr Val Leu Leu Tyr Tyr Ile Arg Val Leu Ile
            20                  25                  30

Ala Lys Thr Ala Arg Asp Ala Gly Ala Leu Arg Gln Gln Arg Ala Ala
        35                  40                  45

Phe Phe Glu Ala Trp Ser Asn Ala Val Ser Leu Arg Asn Leu Lys Asn
50                  55                  60

Val Ala Lys Lys Val Lys Lys Ala Thr Glu Ala Val Asp Trp Ala Thr
65                  70                  75                  80

Gln Cys Glu Gly Val Met Phe Met Thr Leu Gln Thr Ile Ile Arg Ala
                85                  90                  95

Leu Asn Thr Met Arg Gly His Val Ser Asp Lys Asp Gly Thr Ala Pro
            100                 105                 110

Ser Asp Cys Gly Leu Glu Pro His Gln Gly Arg Ala Ala Asp Arg Asn
        115                 120                 125

Met Thr Tyr Val Glu Val Ile Glu His Ile Lys Ser Thr Glu Arg Arg
130                 135                 140

Leu Gln Glu Leu Ser Met Phe Ala Glu Ser Val Arg Thr Phe Tyr
145                 150                 155                 160

Gly Asn Tyr Val Asn Gly Val Gly Leu Leu Asn Asp Thr Asn Asn Tyr
                165                 170                 175

Phe Ala Ala Ala Glu Ala Ala Arg Arg Ala Leu Arg Glu Ala Asp Glu
            180                 185                 190

Ala Met Lys Asp Ala Ser Asp Arg Lys Glu Leu Asn Glu Lys Arg Val
        195                 200                 205

Gln Leu Gly Cys Glu Val Glu Lys Gly Leu Phe Phe Met Arg Glu Ile
    210                 215                 220

Phe Leu Thr Leu His Ser Val Ser Glu Arg Val Ile Ser Arg Glu Arg
225                 230                 235                 240

Ala Leu Lys Ala Lys Val Gly Glu Leu Asp Glu Gly Pro Gly Ala Cys
                245                 250                 255

Gly Met Ala His Thr Met Phe Arg Ser Thr Ala Tyr Ala Asn Leu Arg
            260                 265                 270

Ala Ser Ser Ala Lys Asp Glu Ser Ser Leu Ala Val Val Glu Leu Ser
        275                 280                 285

Glu Phe Met Gly Ile Lys Gly His Ser Thr Leu His His Glu Leu Glu
    290                 295                 300

Tyr Asp Asp Asp Phe Lys Ile Ser Leu Thr Asn Cys Arg Asp Ser Glu
305                 310                 315                 320

Leu Glu Gln Ser Leu Val Phe Arg Phe Ala Arg Gly Glu Glu Asn Asp
                325                 330                 335

Asn Ile Tyr Asp Phe Asp Arg Trp Arg Ala Ala Ala Asp Glu Leu Trp
            340                 345                 350

Asn Lys Val Glu Ser His Thr His Ile Ile Ser Glu Lys Cys Thr Lys
        355                 360                 365
```

```
Val Ser Gly Val Asp Cys Ser Glu Ala Val Gly Ala Val Thr Met Leu
    370                 375                 380

Ile Gly Arg Leu Arg Gln Leu Glu Gly Asp Leu Glu Arg Gly Leu Gly
385                 390                 395                 400

Ala Ala Ile Arg Ala Leu Lys Thr Val Glu Asp Gly Ile Ala Thr Ser
                405                 410                 415

Gln Asp Ala Met Arg Lys Cys Gln His Gly Ala Val Asn Glu His
            420                 425                 430

His Thr Glu Ala Lys Glu Pro Gln Thr Thr Ser Gly Arg Arg Glu Ala
        435                 440                 445

Asn Thr Asp Ser Ala Pro Ala Lys Glu Gln Leu Asp Ala Ala Ser Lys
450                 455                 460

Leu Glu Gly Gly Ser Arg Leu Glu Glu Val Asp Gly Asn Glu Lys
465                 470                 475                 480

Glu Glu Gln Gln Glu Ala Pro Ala Asn Gly Pro Gln Gly Ala Leu Gly
                485                 490                 495

Val Arg Gln Glu Glu Thr Ser Tyr Glu Gly Asp Ala Gly Arg Gly Ser
            500                 505                 510

Val Asp Thr Gly His Asp Glu Phe Ala Thr Tyr Leu Ala Ser Arg Ser
        515                 520                 525

Ala Cys Ser Thr Ala Gly Asp Gly Ile Glu Ser Ser Ser Thr Ala Gly
    530                 535                 540

Asp Ala Ala Ala Val Glu Ala Arg Ser
545                 550

<210> SEQ ID NO 2
<211> LENGTH: 606
<212> TYPE: PRT
<213> ORGANISM: T. vivax

<400> SEQUENCE: 2

Met Leu Ala Tyr Lys Leu Ile Leu Cys Ser Thr Val Phe Leu Leu Cys
1               5                   10                  15

Pro Ile Val Ala Phe Ser Ile Asp Asp Glu Gly Glu Ser Ala Gln Phe
                20                  25                  30

Arg Thr Trp Val Cys Lys Trp Glu Gln Lys Arg Thr Val Leu Leu Tyr
            35                  40                  45

Tyr Ile Arg Val Leu Ile Ala Lys Thr Ala Arg Asp Ala Gly Ala Leu
        50                  55                  60

Arg Gln Gln Arg Ala Ala Phe Phe Glu Ala Trp Ser Asn Ala Val Ser
65                  70                  75                  80

Leu Arg Asn Leu Lys Asn Val Ala Lys Lys Val Lys Lys Ala Thr Glu
                85                  90                  95

Ala Val Asp Trp Ala Thr Gln Cys Glu Gly Val Met Phe Met Thr Leu
            100                 105                 110

Gln Thr Ile Ile Arg Ala Leu Asn Thr Met Arg Gly His Val Ser Asp
        115                 120                 125

Lys Asp Gly Thr Ala Pro Ser Asp Cys Gly Leu Glu Pro His Gln Gly
130                 135                 140

Arg Ala Ala Asp Arg Asn Met Thr Tyr Val Glu Val Ile Glu His Ile
145                 150                 155                 160

Lys Ser Thr Glu Arg Arg Leu Gln Glu Leu Ser Met Phe Ala Glu Glu
                165                 170                 175

Ser Val Arg Thr Phe Tyr Gly Asn Tyr Val Asn Gly Val Gly Leu Leu
            180                 185                 190
```

-continued

```
Asn Asp Thr Asn Asn Tyr Phe Ala Ala Glu Ala Ala Arg Arg Ala
        195                 200                 205

Leu Arg Glu Ala Asp Glu Ala Met Lys Asp Ala Ser Asp Arg Lys Glu
210                 215                 220

Leu Asn Glu Lys Arg Val Gln Leu Gly Cys Glu Val Glu Lys Gly Leu
225                 230                 235                 240

Phe Phe Met Arg Glu Ile Phe Leu Thr Leu His Ser Val Ser Glu Arg
                245                 250                 255

Val Ile Ser Arg Glu Arg Ala Leu Lys Ala Lys Val Gly Glu Leu Asp
                260                 265                 270

Glu Gly Pro Gly Ala Cys Gly Met Ala His Thr Met Phe Arg Ser Thr
                275                 280                 285

Ala Tyr Ala Asn Leu Arg Ala Ser Ser Ala Lys Asp Glu Ser Ser Leu
        290                 295                 300

Ala Val Val Glu Leu Ser Glu Phe Met Gly Ile Lys Gly His Ser Thr
305                 310                 315                 320

Leu His His Glu Leu Glu Tyr Asp Asp Asp Phe Lys Ile Ser Leu Thr
                325                 330                 335

Asn Cys Arg Asp Ser Glu Leu Glu Gln Ser Leu Val Phe Arg Phe Ala
                340                 345                 350

Arg Gly Glu Glu Asn Asp Asn Ile Tyr Asp Phe Asp Arg Trp Arg Ala
                355                 360                 365

Ala Ala Asp Glu Leu Trp Asn Lys Val Glu Ser His Thr His Ile Ile
        370                 375                 380

Ser Glu Lys Cys Thr Lys Val Ser Gly Val Asp Cys Ser Glu Ala Val
385                 390                 395                 400

Gly Ala Val Thr Met Leu Ile Gly Arg Leu Arg Gln Leu Glu Gly Asp
                405                 410                 415

Leu Glu Arg Gly Leu Gly Ala Ala Ile Arg Ala Leu Lys Thr Val Glu
                420                 425                 430

Asp Gly Ile Ala Thr Ser Gln Asp Ala Met Arg Lys Cys Gln His Gly
        435                 440                 445

Gly Ala Val Asn Glu His His Thr Glu Ala Lys Glu Pro Gln Thr Thr
450                 455                 460

Ser Gly Arg Arg Glu Ala Asn Thr Asp Ser Ala Pro Ala Lys Glu Gln
465                 470                 475                 480

Leu Asp Ala Ala Ser Lys Leu Glu Gly Gly Ser Arg Leu Glu Glu Glu
                485                 490                 495

Val Asp Gly Asn Glu Lys Glu Gln Gln Glu Ala Pro Ala Asn Gly
                500                 505                 510

Pro Gln Gly Ala Leu Gly Val Arg Gln Glu Glu Thr Ser Tyr Glu Gly
        515                 520                 525

Asp Ala Gly Arg Gly Ser Val Asp Thr Gly His Asp Glu Phe Ala Thr
530                 535                 540

Tyr Leu Ala Ser Arg Ser Ala Cys Ser Thr Ala Gly Asp Gly Ile Glu
545                 550                 555                 560

Ser Ser Ser Thr Ala Gly Asp Ala Ala Ala Val Glu Ala Arg Ser Lys
                565                 570                 575

Lys Lys Tyr Leu Ala Leu Met Ser Val Leu Cys Phe Leu Phe Val Ser
                580                 585                 590

Ala Ala Ser Val Val Leu Leu Ala Trp Lys Arg Thr Lys Leu
        595                 600                 605
```